United States Patent
Goklen et al.

(10) Patent No.: US 7,241,866 B2
(45) Date of Patent: Jul. 10, 2007

(54) USING AMINES OR AMINO ACIDS AS MOBILE PHASE MODIFIERS IN CHROMATOGRAPHY

(75) Inventors: Kent E. Goklen, Fanwood, NJ (US); Joseph Nti-Gyabaah, Somerset, NJ (US); Firoz D. Antia, Montclair, NJ (US); Mary Ellen Dahlgren, Metuchen, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/526,301

(22) PCT Filed: Oct. 24, 2003

(86) PCT No.: PCT/US03/33978

§ 371 (c)(1),
(2), (4) Date: Mar. 1, 2005

(87) PCT Pub. No.: WO2004/042350

PCT Pub. Date: May 21, 2004

(65) Prior Publication Data

US 2006/0014933 A1    Jan. 19, 2006

Related U.S. Application Data

(60) Provisional application No. 60/422,356, filed on Oct. 30, 2002.

(51) Int. Cl.
*C07K 1/00*    (2006.01)

(52) U.S. Cl. .................................................... 530/350
(58) Field of Classification Search ................ 530/344, 530/350
See application file for complete search history.

(56) References Cited

U.S. PATENT DOCUMENTS

| 4,784,988 A |   | 11/1988 | Bruzzese et al. |
| 4,812,442 A |   | 3/1989 | Boger et al. |
| 5,194,377 A |   | 3/1993 | Schwartz et al. |
| 5,202,309 A |   | 4/1993 | Schwartz et al. |
| 6,130,353 A | * | 10/2000 | Bopp ........................ 562/401 |
| 6,153,590 A |   | 11/2000 | Andersen et al. |

FOREIGN PATENT DOCUMENTS

JP    11023558 A    1/1999

OTHER PUBLICATIONS

D.J. Roush et al., "Preparative High-Performance Liquid Chromatography of Echinocandins"1998, vol. 827, pp. 373-389, J. of Chromatography A.

* cited by examiner

*Primary Examiner*—Karen Cochrane Carlson
*Assistant Examiner*—Agnes B. Rooke
(74) *Attorney, Agent, or Firm*—Julie M. Lake; Sheldon O. Heber

(57) ABSTRACT

This invention relates to the use of amine, amino acid and amino acid ester mobile modifiers in normal phase chromatography to improve the resolution and or productivity of peptide and lipopeptide purification. This chromatographic method can be sued for either analytical or preparative scale purification.

17 Claims, 12 Drawing Sheets

USING AMINES OR AMINO ACIDS AS MOBILE PHASE MODIFIERS IN CHROMATOGRAPHY

CROSS REFERENCE TO RELATED APPLICATIONS

This application is a U.S. National Stage of International Application No. PCT/US03/33978 filed on Oct. 24, 2003, which claims priority under 35 USC 119(e) from U.S. Provisional Application No. 60/422,356 filed on Oct. 30, 2002.

FIELD OF THE INVENTION

This invention relates to the use of amines, amino acids or amino acid esters as mobile phase modifiers in normal phase chromatography of peptide and lipopeptide compounds.

BACKGROUND OF THE INVENTION

In the past, the resolution of key impurities such as Pneumocandins $B_5$ and $E_0$ from Pneumocandin $B_0$ in the silica gel HPLC purification was poor. Some analogs were only partially resolved from the main product peak under preparative conditions. To achieve the desired product purity, the limited resolution required that the purification step be run at low column loading, which limited productivity.

Lipopeptides, such as Pneumocandin $B_0$, are often the product of a fermentation process. During such a fermentation process, many very closely related analogues are produced along with the desired product. Normal phase chromatography systems are frequently used to purify the crude fermentation product. A normal phase chromatography system usually consists of a stationary phase and a mobile phase. For purification of a peptide or lipopeptide, the stationary phase can be silica gel or alumina, and the mobile phase can be a single solvent or a mixture of solvents, which includes organic solvents and water.

Silica gel chromatography and other types of normal phase chromatography are useful for separating these analogues. However, in practice, the resolution of certain close analogues from the desired product is often poor and not satisfactory, because the resolution is not great and often there is overlap. To achieve the desired purity of the main product at a reasonable yield requires restricting the amount of material (often referred to as feed or column load) loaded onto the column per run, which limits the productivity of the operation.

The purification of Pneumocandin $B_0$ falls into this category. The chromatography utilizes a mobile phase consisting of a mixture of solvents, specifically ethyl acetate (EtOAc), methanol (MeOH) and water, on a silica gel column. Pneumocandin $B_0$, with a molecular weight of 1065 Daltons, is a natural product and serves as an intermediate in the production of Caspofungin acetate (Cancidas®). Pneumocandin $B_0$ is produced as a secondary metabolite by fermentation of the fungus *Glarea lozoyensis*. See U.S. Pat. Nos. 5,194,377 and 5,202,309. The structures of Pneumocandin $B_0$ and two of the key analog impurities, all comprised of a cyclic hexapeptide coupled with dimethylmyristate side chain, are shown in Formula I and Table 1.

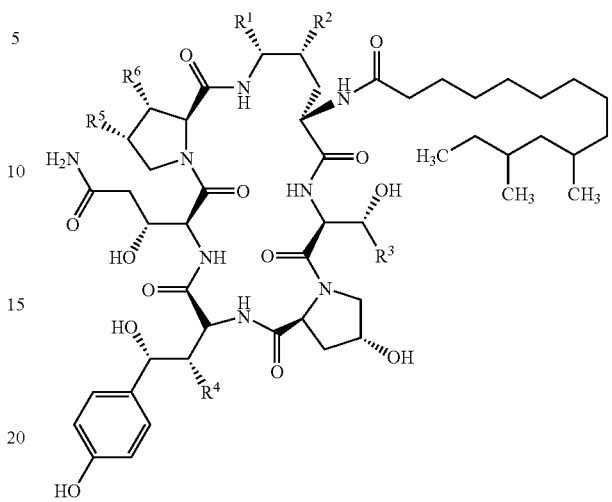

Formula I

TABLE 1

Pneumocandin $B_0$ and two of its analogs

| Compound | $R^1$ | $R^2$ | $R^3$ | $R^4$ | $R^5$ | $R^6$ |
|---|---|---|---|---|---|---|
| Pneumocandin $B_0$ | OH | OH | Me | OH | H | OH |
| Pneumocandin $B_5$ | OH | H | Me | OH | H | OH |
| Pneumocandin $E_0$ | OH | OH | Me | OH | H | H |

Silica gel chromatography exploits the subtle variations in binding affinity of the hydroxy-rich cyclic hexapeptide core of the desired product and the analog impurities, including Pneumocandins $B_5$ and $E_0$, to effect a separation. In the silica gel HPLC purification, Pneumocandins $B_5$ and $E_0$, two of the key analog impurities co-produced in the fermentation of Pneumocandin $B_0$, elute very close to Pneumocandin $B_0$. Therefore, to meet the target impurity levels in the purified material for these and similar analog compounds, the quantity of crude Pneumocandin $B_0$ that can be loaded onto the column is limited. As a result, significant efforts have been made to improve the resolution of key impurities. For instance, the ternary ethyl acetate-methanol-water mobile phase has been balanced to optimize resolution between Pneumocandin $B_0$ and key analog impurities. D. J. Roush, F. D. Antia, K. E. Göklen *J. Chromatography* A, 827 (1998) 373-389.

SUMMARY OF THE INVENTION

This invention discloses the use of mobile phase modifiers, including amino acids, amino acid esters or amines, during the HPLC purification of a lipopeptide or peptide. The mobile phase modifiers bind to the stationary phase and modify the binding characteristics of the stationary phase improving the resolution and or purification of desired lipopeptide or peptide from its related impurities.

This invention is useful in analytical chromatography and even more valuable for preparative chromatography (i.e., using chromatography as a large-scale purification technique). Specifically, amino acids, amino acid esters or amines can be used as mobile phase modifiers in the chromatographic purification of peptides or lipopeptides, for example the purification of Pneumocandin $B_0$, which is the natural product starting material (a fermentation product) used to prepare Caspofungin acetate (Cancidas®). The invention would also be useful in purifying the fermentation product precursor for other lipopeptides, such as Micafungin, Anidulafungin, Cilofungin and Daptomycin.

BRIEF DESCRIPTION OF THE DRAWINGS

Preparative HPLC chromatogram of silica gel chromatography of crude Pneumocandin $B_0$, where the column feed contains a small amount of proline. FIG. 1A. First run on the column. FIG. 1B. Eighteenth run on the column. Improved resolution of analogue impurities is seen in the later run due to the adsorption of proline from the feed solution onto the column.

FIG. 2A. Plot of retention time of Pneumocandin $B_0$ after injecting proline-containing solution onto the column, showing increased retention time, which returns to the original retention time, as the proline is slowly desorbed from the column. FIGS. 2B and 2C. Chromatogram of a typical run just before (2B) and after (2C) injecting proline onto the column. (analytical scale 5 µ YMC silica column using 87/9/7 v/v/v ethyl acetate/methanol/water).

Silica gel HPLC chromatograms for Pneumocandin $B_0$ crude eluted with mobile phase: (3A) without L-proline, (3B) with 0.26 mM L-proline added, and (3C) with 0.65 mM L-proline added. Demonstrates increased retention time of Pneumocandin $B_0$ and increased resolution from analog impurities with increasing levels of proline added. (Pneumocandin $B_0$ retention time is 22 minutes with 0.65 mM L-proline).

FIG. 4

Silica gel BPLC chromatogram for Pneumocandin $B_0$ crude eluted using 20% ethyl acetate and 80% 87/9/7 v/v/v ethyl acetate/methanol/water as the mobile phase. This mobile phase mixture results in increased retention time of Pneumocandin $B_0$, but without the improved resolution from its analogs observed when proline is added to the mobile phase (see FIG. 3). (Pneumocandin $B_0$ retention time is 23 minutes).

FIGS. 5A through 11B

Silica gel HPLC chromatograms for Pneumocandin $B_0$ crude eluted (A) without mobile phase modifier (control) and (B) with the addition of various amino acids to the mobile phase. Demonstrates that addition of all the amino acids have an affect on the Pneumocandin $B_0$ retention and/or its resolution from its analogs. (analytical scale 5 µ YMC silica column using 87/9/7 v/v/v ethyl acetate/methanol/water).

Figure 5A:
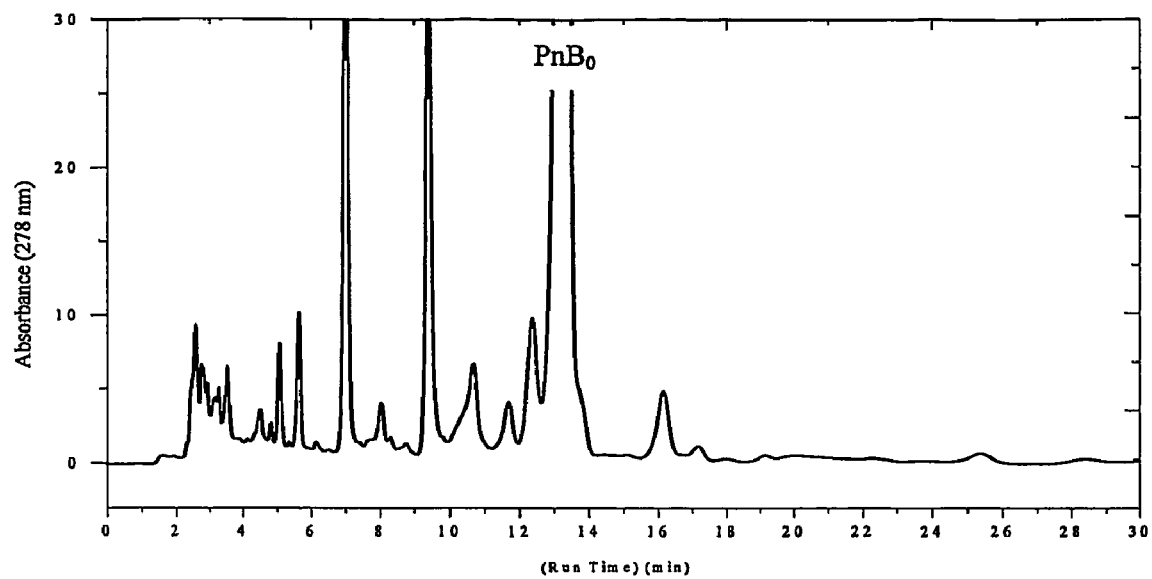
Figure 5B:
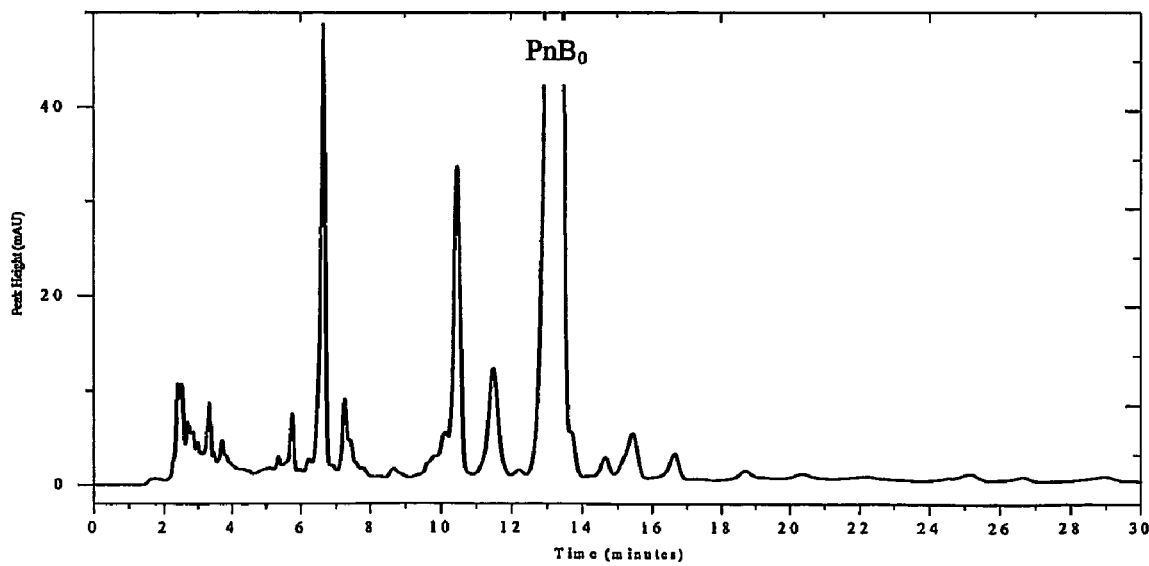

FIGS. 5A and 5B

FIG. 5A. Control prior to exposure of column to trans-4-hydroxyl-L-proline.

FIG. 5B. Chromatogram after exposure of column to mobile phase modified with trans-4-hydroxyl-L-proline, showing similar retention time of Pneumocandin $B_0$ to the control, but different resolution from its analog impurities.

Figure 6A:
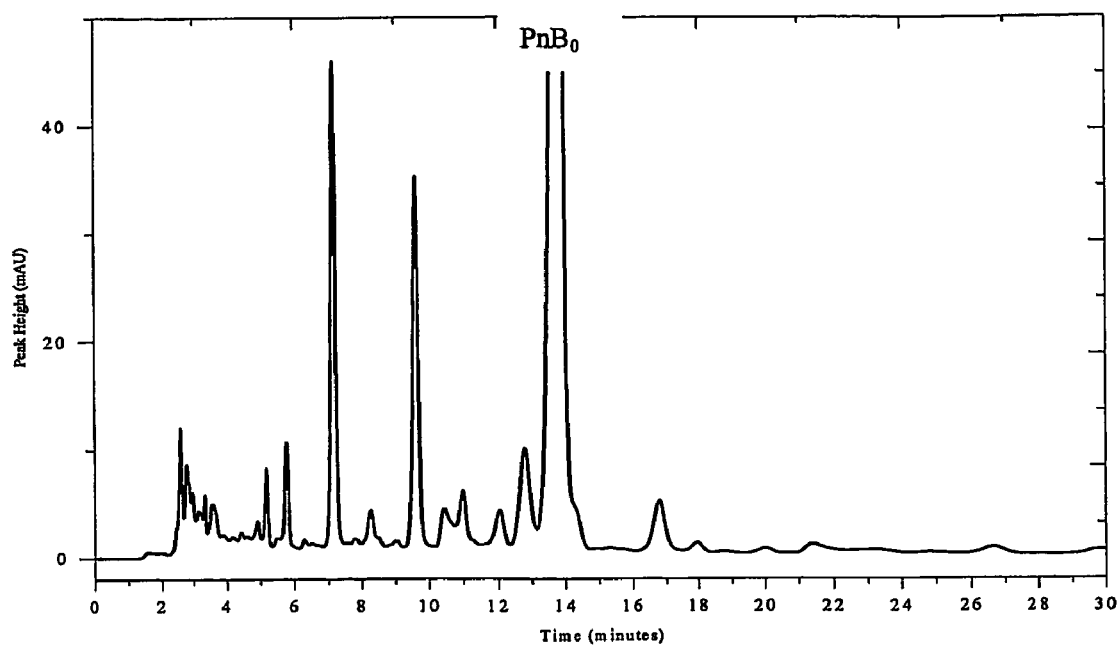
Figure 6B:
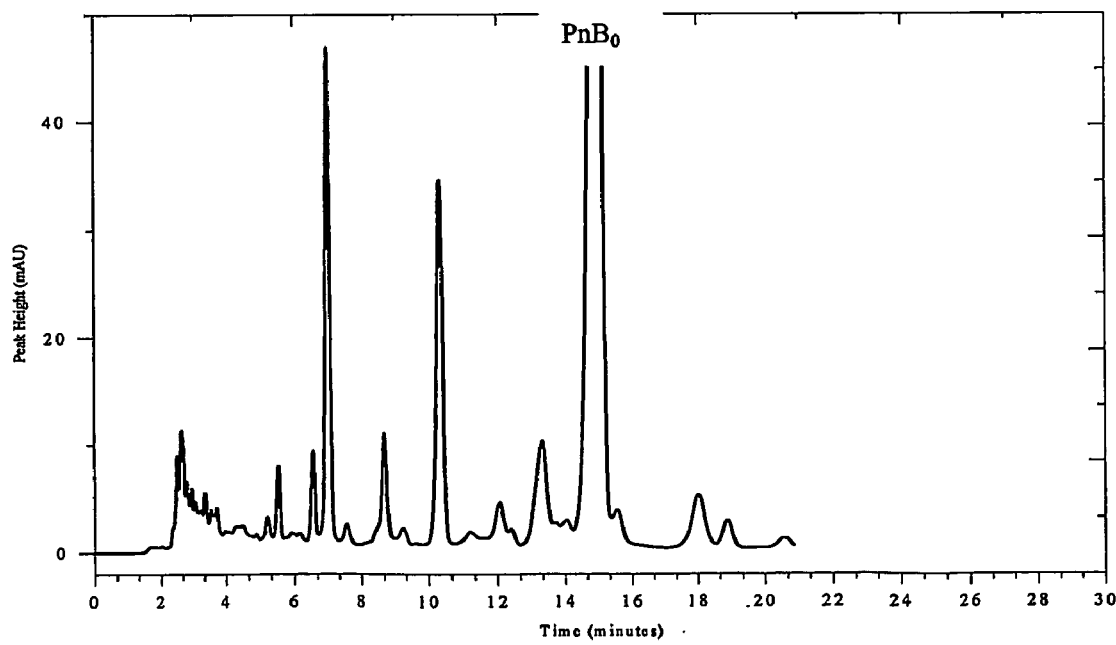

FIGS. 6A and 6B.

FIG. 6A. Control prior to exposure of column to L-valine.

FIG. 6B. Chromatogram after exposure of the column to mobile phase modified with L-valine, showing changes from the control in both the retention time of Pneumocandin $B_0$ and the resolution from its analog impurities.

Figure 7A:
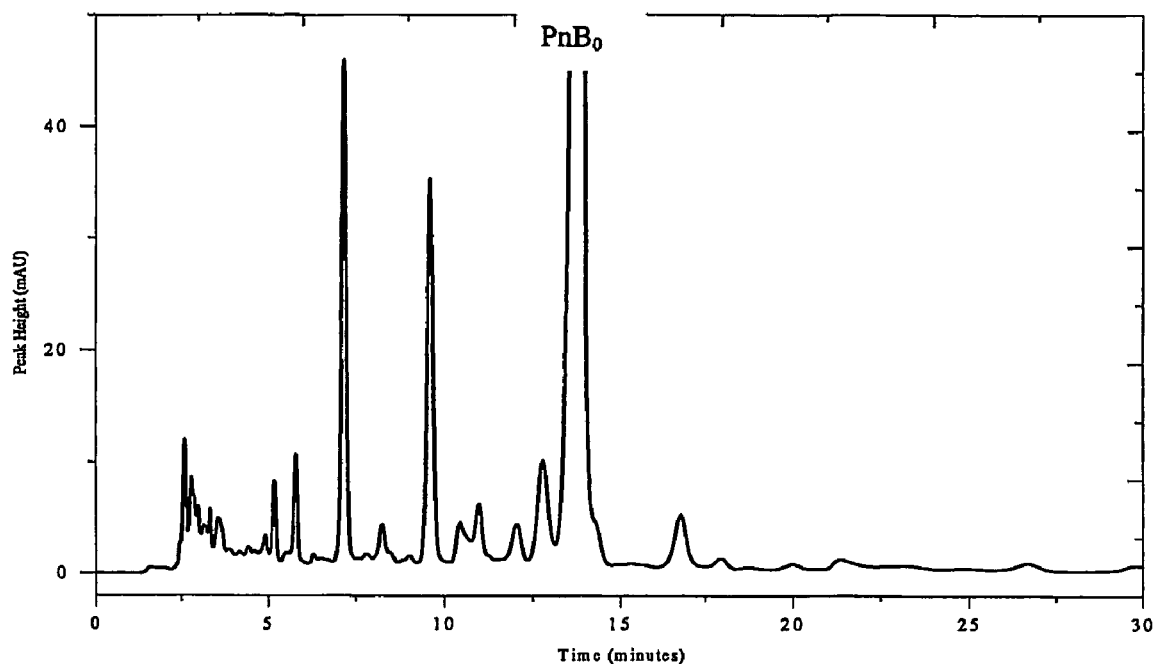
Figure 7B:
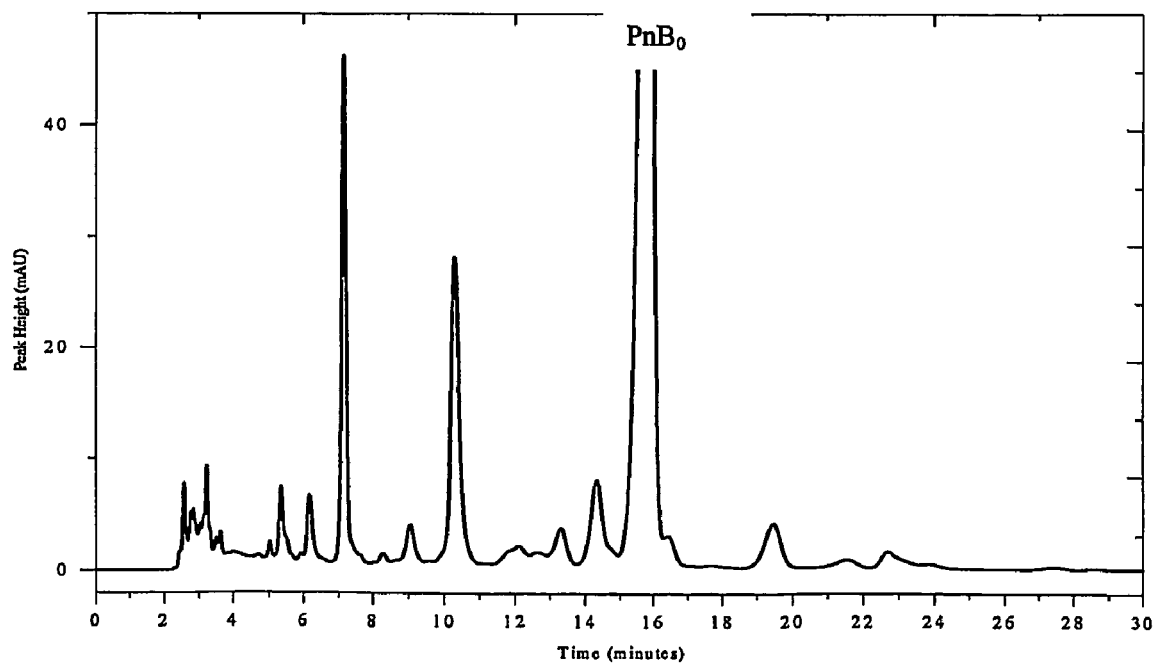

FIGS. 7A and 7B

FIG. 7A. Control prior to exposure of column to L-lysine.

FIG. 7B. Chromatogram after exposure of the column to mobile phase modified with L-lysine, showing changes from the control in both the retention time of Pneumocandin $B_0$ and the resolution from its analog impurities.

Figure 8A:
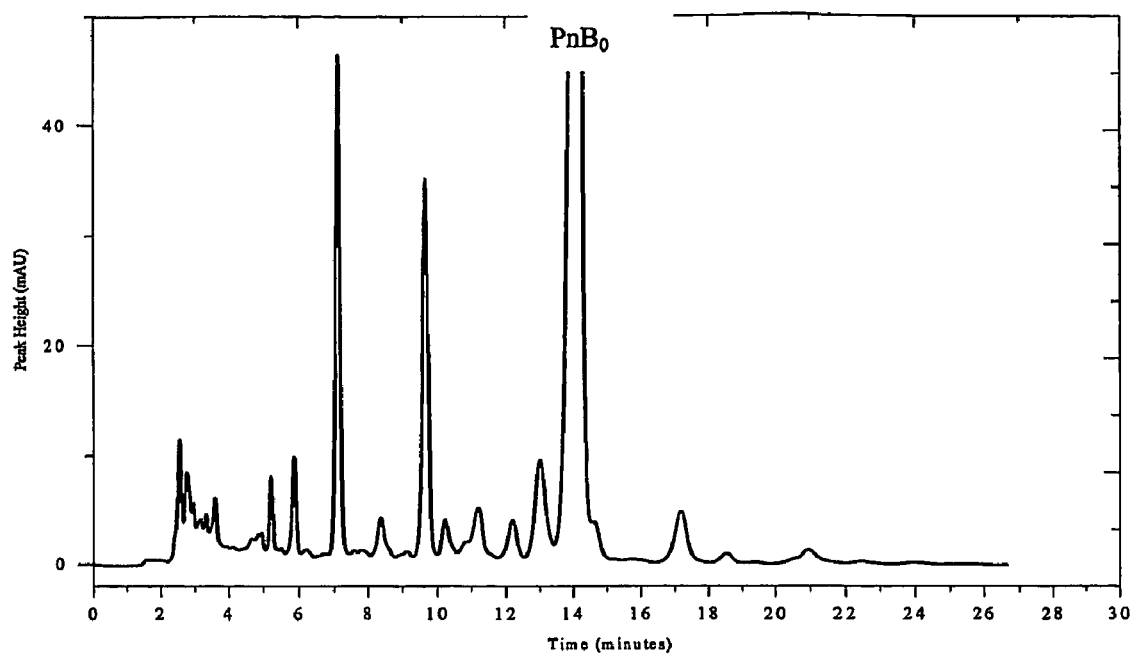
Figure 8B:
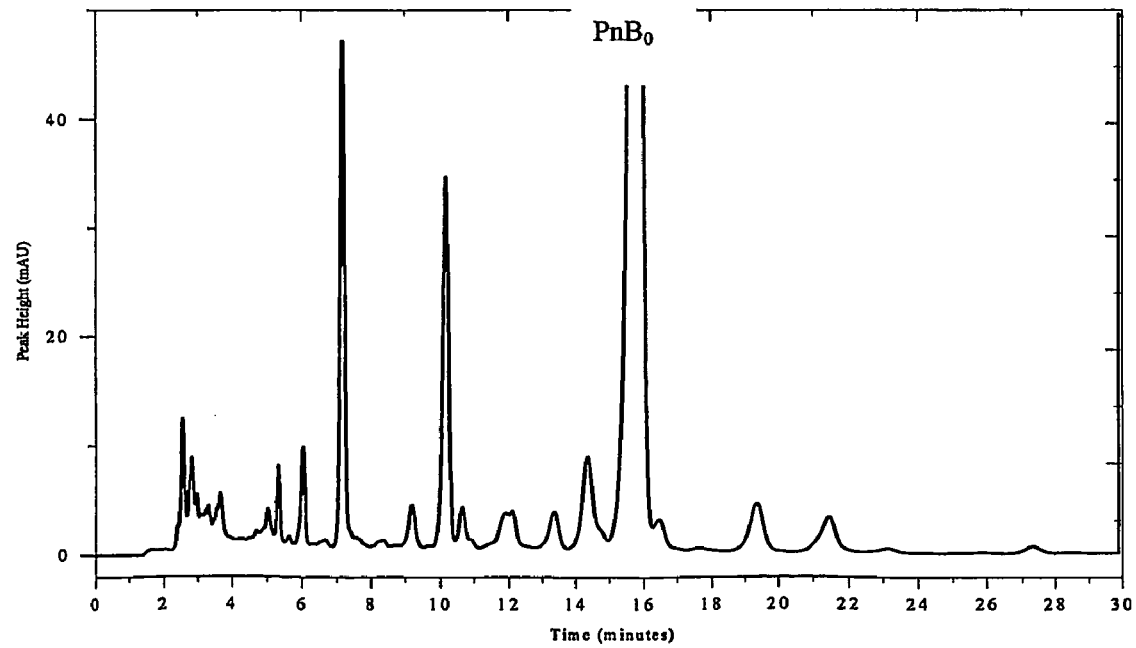

FIGS. 8A and 8B

FIG. 8A. Control prior to exposure of column to L-methionine.

FIG. 8B. Chromatogram after exposure of the column to mobile phase modified with L-methionine, showing changes from the control in both the retention time of Pneumocandin $B_0$ and the resolution from its analog impurities.

Figure 9A:
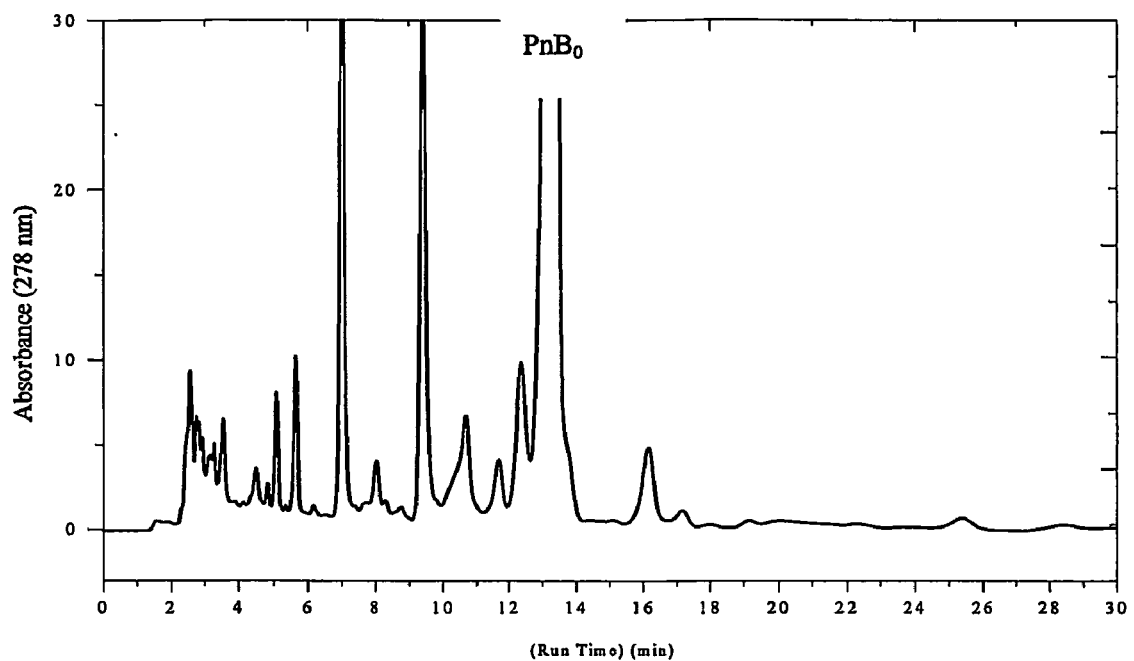
Figure 9B:
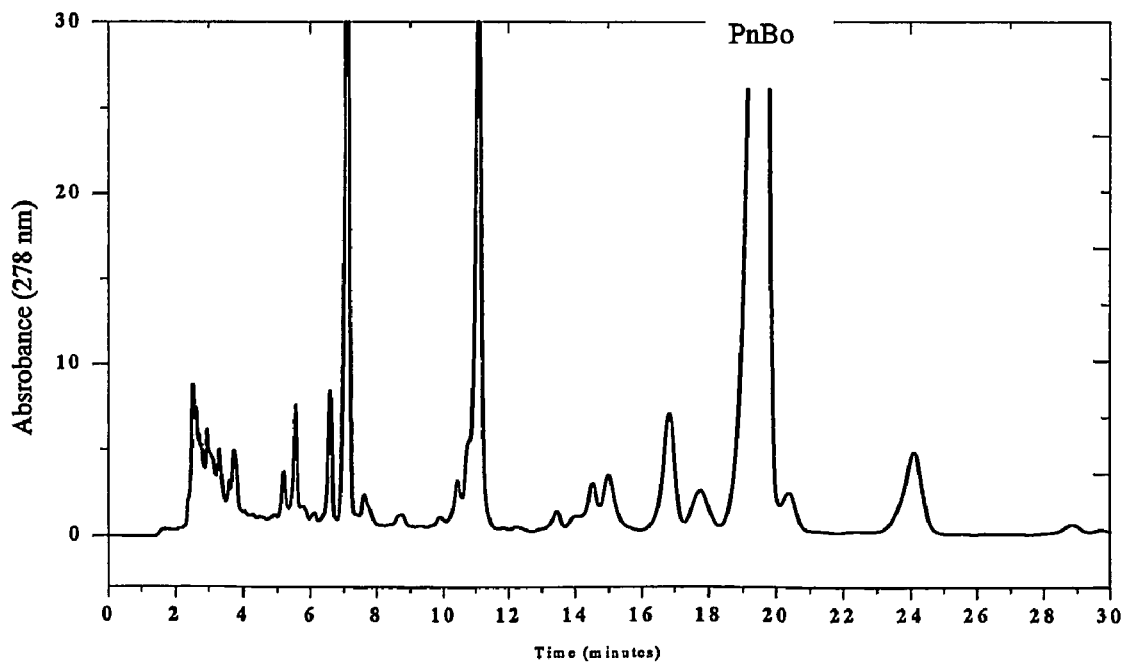

FIGS. 9A and 9B.

FIG. 9A. Control prior to exposure of column to D-proline.

FIG. 9B. Chromatogram after exposure of the column to mobile phase modified with D-proline, showing changes from the control in both the retention time of Pneumocandin $B_0$ and the resolution from its analog impurities.

Figure 10A:
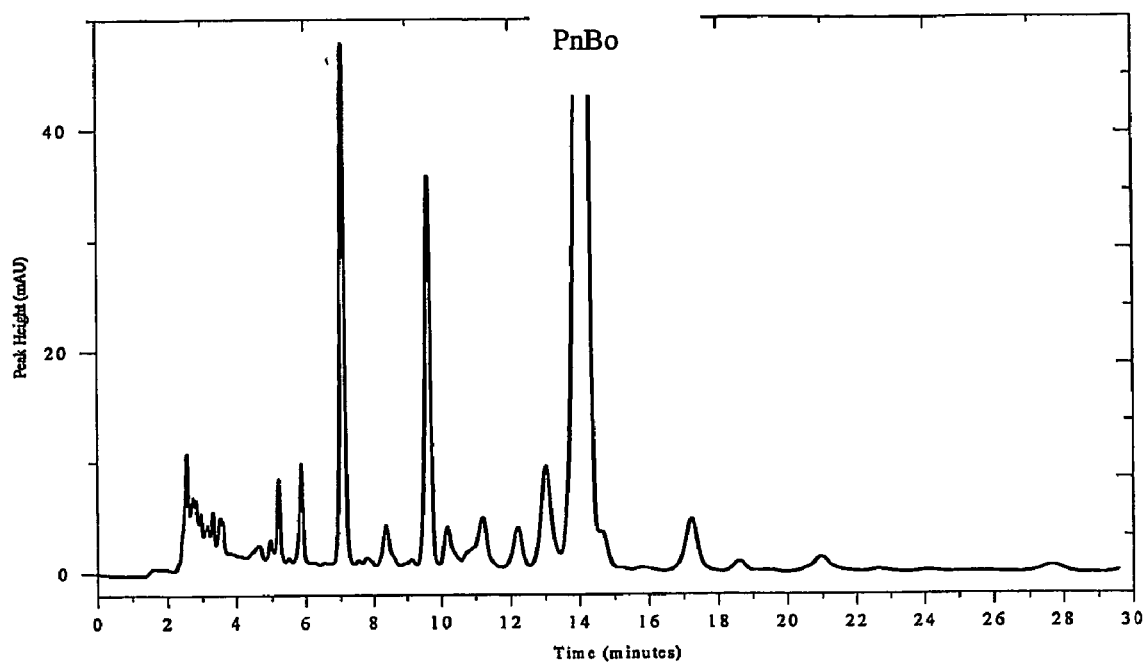
Figure 10B:
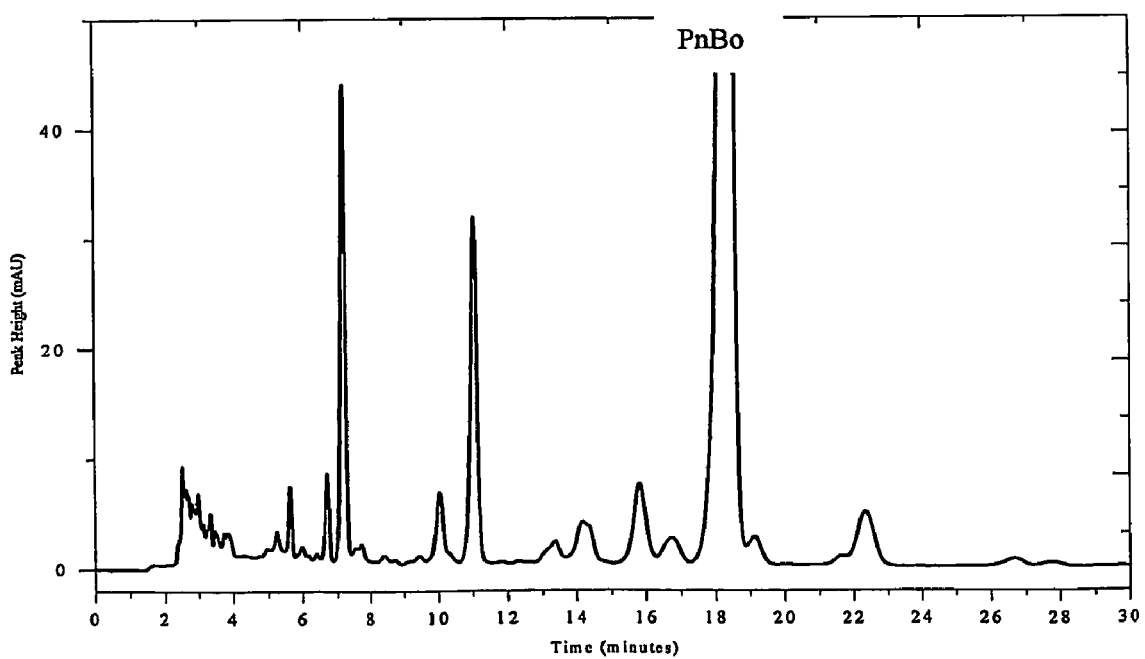

FIGS. 10A and 10B

FIG. 10A. Control prior to exposure of column to L-threonine.

FIG. 10B. Chromatogram after exposure of the column to mobile phase modified with L-threonine, showing changes from the control in both the retention time of Pneumocandin $B_0$ and the resolution from its analog impurities.

Figure 11A:
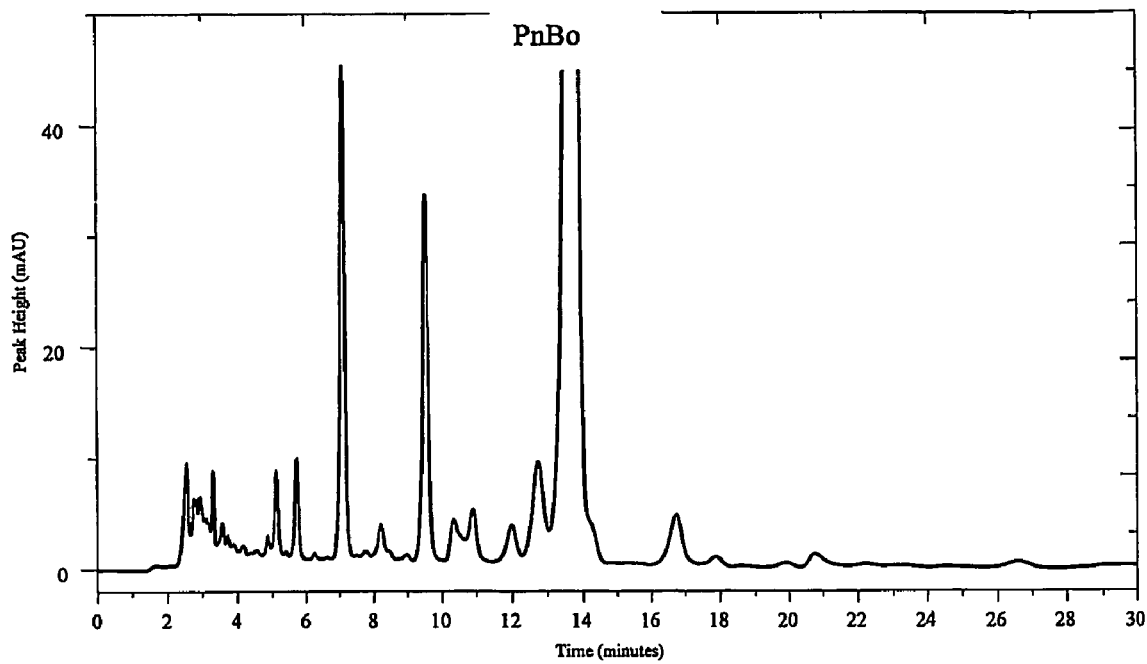
Figure 11B:
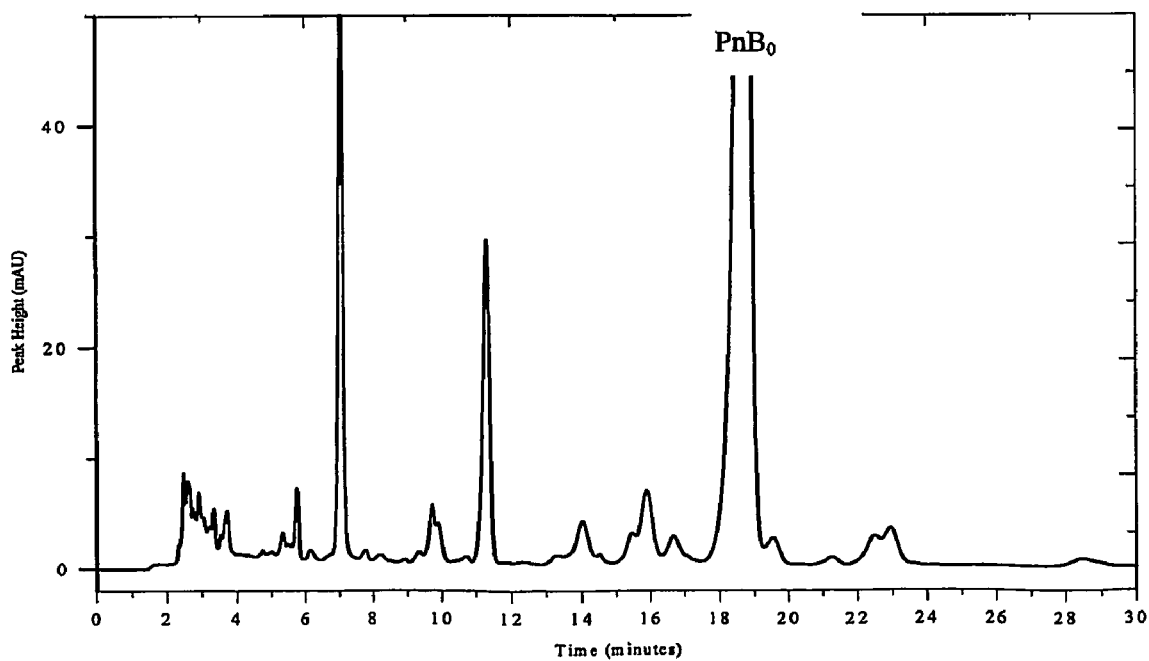

FIGS. 11A and 11B.

FIG. 11A. Control prior to exposure of column to glycine.

FIG. 11B. Chromatogram after exposure of the column to mobile phase modified with glycine, showing changes from the control in both the retention time of Pneumocandin $B_0$ and the resolution from its analog impurities.

Figure 12A:
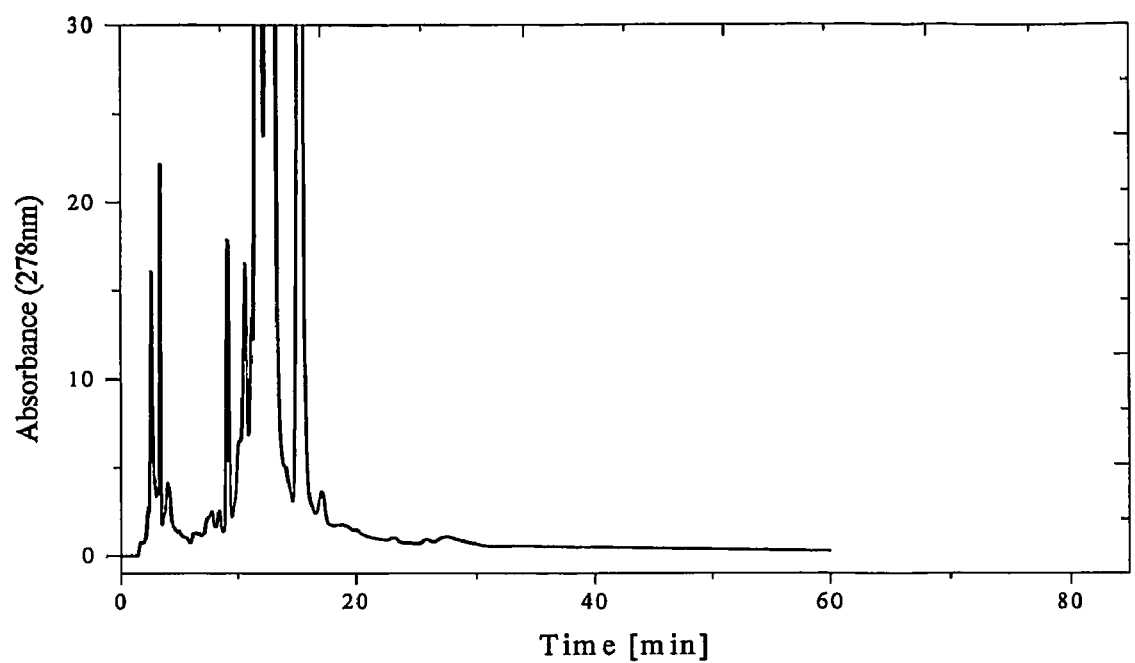
Figure 12B:
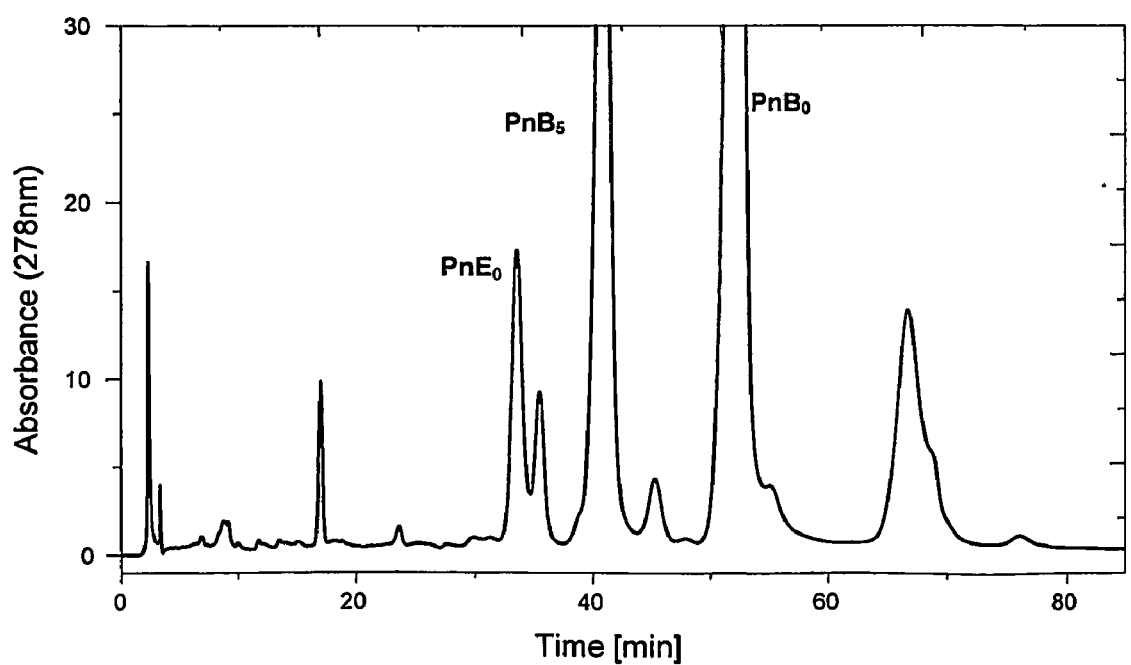

FIGS. 12A and 12B

Silica gel HPLC chromatograms for Pneumocandin $B_0$ crude eluted (A) without (control) and (B) with the addition of diethylamine to the mobile phase. Demonstrates that diethylamine addition has a very strong affect on the Pneumocandin $B_0$ retention and its resolution from its analogs. (analytical scale 5µ YMC silica column using 87/9/7 v/v/v ethyl acetate/methanol/water).

DETAILED DESCRIPTION OF THE INVENTION

A method for the purification of a peptide or a lipopeptide by using a mobile phase modifier in a normal phase chromatography system to improve the selectivity and/or productivity of the purification is disclosed. The method as recited above, wherein the mobile phase modifier is selected from a group consisting of an amine, an amino acid or an amino acid ester. The method as recited above, wherein the normal phase chromatography system includes a mobile phase and a stationary phase. The method as recited above, wherein the stationary phase is selected from silica gel and alumina. The method as recited above, wherein the mobile phase is a solvent system comprising one or more solvents. The method as recited above, wherein the mobile phase modifier is an amine. The method as recited above, wherein the amine is a primary, secondary, or tertiary amines, including lower alkyl ($C_1$-$C_6$ alkyl) amines, lower dialkyl ($C_1$-$C_6$ alkyl) amines and/or aromatic ($C_6$-$C_{10}$ aryl) amines. Examples of amines, which are useful in the method, as recited above are methylamine, ethylamine, diisopropylamine, diethylamine, dimethylamine, ethylmethylamine, triethylamine, propylamine, aniline and dimethylaniline. The method as recited above, wherein the mobile phase modifier is an amino acid or amino acid ester. The method as recited above, wherein the amino acid or amino acid ester mobile phase modifier is selected from the group consisting of: L-amino acids, D-amino acids, L-amino acid esters and D-amino acid esters. The method as recited above, wherein the amino acid or amino acid ester mobile phase modifier is selected from: L-proline, D-proline, trans-4-hydroxy-L-proline, trans4-hydroxy-D-proline, glycine, L-threonine, D-threonine, L-lysine, D-lysine, L-methionine, D-methionine, D-valine, L-valine and esters of the aforementioned band D-amino acids. The method as recited above, wherein the amino acid is selected from: L-proline and D-proline.

An embodiment of the invention is the method of purifying a peptide or a lipopeptide by using an amine or amino acid mobile phase modifier in a normal phase chromatography system with a stationary phase of alumina or silica gel to improve the resolution and/or productivity of the purification, wherein the purification is of a peptide. Examples of peptides are linear and cyclic amino acid chains under 1800 molecular weight, formed by the combination of the amino group of one amino acid with the carboxyl group of another in an amide bond, and produced as secondary metabolites of microorganisms. Other examples of peptides are oxytocin and bradykinin.

A further embodiment of the invention is the method of purifying a peptide or a lipopeptide by using an amine or amino acid mobile phase modifier in a normal phase chromatography system with a stationary phase of alumina or silica gel to improve the resolution and/or productivity of the purification, wherein the purification is of a lipopeptide. The method as recited above, wherein the lipopeptide is selected from a fermentation product precursor of Caspofungin, Micafungin Andulifungin, Cilofungin, and Daptomycin. The method as recited above, wherein the lipopeptide is pneumocandin $B_0$. The method as recited above, wherein the mobile phase modifier is an amine. The method as recited above, wherein the amine mobile phase modifier is selected from the group consisting of: methylamine, ethylamine, diisopropylamine, diethylamine, dimethylamine, ethylmethylamine, triethylamine, propylamine, aniline and dimethylaniline. The method as recited above, wherein the mobile phase modifier is an amino acid or amino acid ester. The method as recited above, wherein the amino acid or amino acid ester mobile phase modifier is selected from the group consisting of: L-amino acids, D-amino acids, L-amino acid esters and D-amino acid esters. The method as recited above, wherein the stationary phase is silica gel. The method as recited above, wherein the amino acid or amino acid ester mobile phase modifier is selected from: L-proline, D-proline, trans-4-hydroxy-L-proline, trans-4-hydroxy-D-proline, glycine, L-threonine, D-threonine, L-lysine, D-lysine, L-methionine, D-methionine, D-valine, L-valine and esters of the aforementioned b-and D-amino acids. The method as recited, wherein the mobile phase is a solvent system comprising water, methanol, and ethyl acetate. The method as recited above, wherein the amino acid mobile phase modifier is selected from: L-proline and D-proline.

Yet another embodiment of the invention is the method of purifying a peptide or a lipopeptide by using an amine or amino acid mobile phase modifier in a normal phase chromatography system with a stationary phase of alumina or silica gel to improve the resolution and/or productivity of the purification, wherein the purification is of a peptide. The method as recited above, wherein the mobile phase modifier is an amine. The method as recited above, wherein the mobile phase modifier is an amino acid or amino acid ester. The method as above, wherein the stationary phase is silica gel.

Examples of lipopeptides, for which this purification process is useful, are echinocandin derivatives, such as Pneumocandin $B_0$, Caspofungin, Cilofungin and Micafungin as well as Anidulafungin and Daptomycin, and particularly the natural product precursors of Caspofungin, Micafungin, Cilofungin, Anidulafungin and Daptomycin. The natural product/fermentation product precursor for Caspofungin is Pneumocandin $B_0$. Caspofungin acetate (CANCIDAS) is a semisynthetic lipopeptide echinocandin B derivative currently being sold in the US as an antifungal agent for intravenous administration. Anidulafungin is a semisynthetic lipopeptide echinocandin B derivative under development by Eli Lilly/Versicor as an antifungal agent for intravenous administration. Anidulafungin is disclosed in U.S. Pat. Nos. 5,965,525 and 6,384,013, hereby incorporated by reference. Cilofungin is an echinocandin lipopeptide disclosed by Eli Lilly in U.S. Pat. No. 4,293,489 for use as an antifungal agent, hereby incorporated by reference. Micafungin (FUNGARD) is an echinocandin-like lipopeptide under development by Fujisawa, as an antifungal agent for intravenous administration. Micafungin is disclosed in U.S. Pat. No. 6,107,458 hereby incorporated by reference. Daptomycin (CIDECIN) is a semisynthetic lipopeptide derivative under development by Cubist as an antibacterial agent. Daptomycin is disclosed by Eli Lilly in U.S. Pat. No. 4,537,717 hereby incorporated by reference.

A normal phase chromatography system employs a mobile phase and a stationary phase. The mobile phase is a solvent system comprising one or more solvents, the composition of which is either constant through out the purification process, or a gradient, where the solvent composition is changed over time during the purification process. The mobile phase solvents include, but are not limited to, water, methanol, ethanol, isopropanol, hexane, ethyl acetate, acetonitrile, and methylene chloride. The stationary phase is selected from silica gel and alumina. The instant invention provides a chromatographic purification method for a peptide or lipopeptide, which employs the addition of a mobile phase modifier to the mobile phase. A column volume is defined, as the volume of solvent needed to traverse the column. Column load (also referred to as column feed or feed load) refers to the amount of material (crude lipopeptide or peptide) that can be purified at one time. The mobile phase modifier is defined as an amino acid, an amino acid ester, or amine. The instant invention contemplates the addition of the mobile phase modifier either to the eluant (mobile phase solvent system) or as a supplement to the column load. Examples of the amino acids contemplated by the invention are any natural or unnatural amino acids, including both L- and D-configurations. Embodiments of the amino acid mobile phase modifiers useful in this process are L- and D-proline, trans-4-hydroxy-L-proline, glycine, L-threonine, L-lysine, L-methionine and L-valine. Examples of amine mobile phase modifiers contemplated by the invention are primary, secondary, or tertiary lower alkyl ($C_1$-$C_6$ alkyl) and/or aromatic ($C_6$-$C_{10}$ aryl) amines. Examples of such amines are methylamine, ethylamine, diisopropylamine, diethylamine, dimethylamine, ethylmethylamine, triethylamine, propylamine, aniline and dimethylaniline.

This invention shows that adding low concentrations of certain amines, amino acids, or amino acid esters to the mobile phase can shift the resolution and selectivity of the system, providing significant enhancement. In particular, the addition of proline to the EtOAc-MeOH-water mixture used in the silica gel chromatography of Pneumocandin $B_0$ significantly increases the resolution of the compound from closely related impurities, including Pneumocandins $B_5$ and $E_0$. This increased resolution allows the loading of the product onto the column to be significantly increased, by a factor of 2 to 3-fold, while maintaining the purity of the product rich cut and the yield. Larger amounts of product can be purified to the same purity at the same yield on the same column of silica using less solvent and in less time. It has also been demonstrated that the presence of the mobile phase modifier in the column load will have a similar effect.

Solvents purchased from Fisher Scientific (Pittsburgh, Pa., USA) were used. Analytical scale HPLC columns (250×4.6 mm id) packed with regular bare silica, 5 μm particle size and 120 Å pore diameter, were obtained from YMC (Wilmington, N.C., USA). The semi-preparative scale experiment employed irregular silica from Amicon (Beverly, Mass., USA) designated Grade 631, Si-60 of nominal particle size 20 μm. For analytical scale experiments, all solvents in the ternary mobile phase and the feed diluent (ethyl acetate, methanol and water) were HPLC grade. Mobile phase employed for the semi-preparative experiment was prepared from methanol (99.9% w/w purity) from Enron (Houston, Tex., USA) and urethane grade ethyl acetate from Eastman (Perth Amboy, N.J., USA) and low ion water produced in the laboratory using a purification unit from Osmonics (Minnetonka, Minn., USA). For both the analytical and semi-prep scale experiments, the mobile phase composition was 87/9/7 (v/v/v) ethyl acetate/methanol/water. Volumetric compositions of solutions do not account for non-ideal mixing effects. For the sake of convenience, the mobile phase will be referred to as WEAM (water/ethyl acetate/methanol). The feed used for the experiments contained Pneumocandin $B_0$ dissolved in a solvent blend of 79.3/13.3/7.4, v/v/v ethyl acetate/methanol/water. L-proline was obtained from Kyowa Hakko Kogyo Ltd. (Japan). Glycine, L-threonine, D-proline, L-methionine, L-lysine, L-valine, trans-4-hydroxy-L-proline, diethyl amine and proline methyl ester were obtained from Sigma-Aldrich Cheme Gmbh (Steinheim, Germany).

Analytical scale experiments were performed on a Hewlett Packard (Waldbronn, Germany) HP1100 HPLC system with column thermostat and variable wavelength detector (VWD) with detection monitored at 278 nm. Semi-preparative experiments employed a Dorr Oliver Model C (1 LPM pumping skid, Biotage Division of Dyax) and a 50 cm×6 cm id axial compression column from Prochrom (Indianapolis, Ind.).

The modifier effect was first observed during the purification of a particular batch of crude Pneumocandin $B_0$ product containing L-proline, which had been added into the fermentation mixture to facilitate the fermentation process.

Figure 1A:
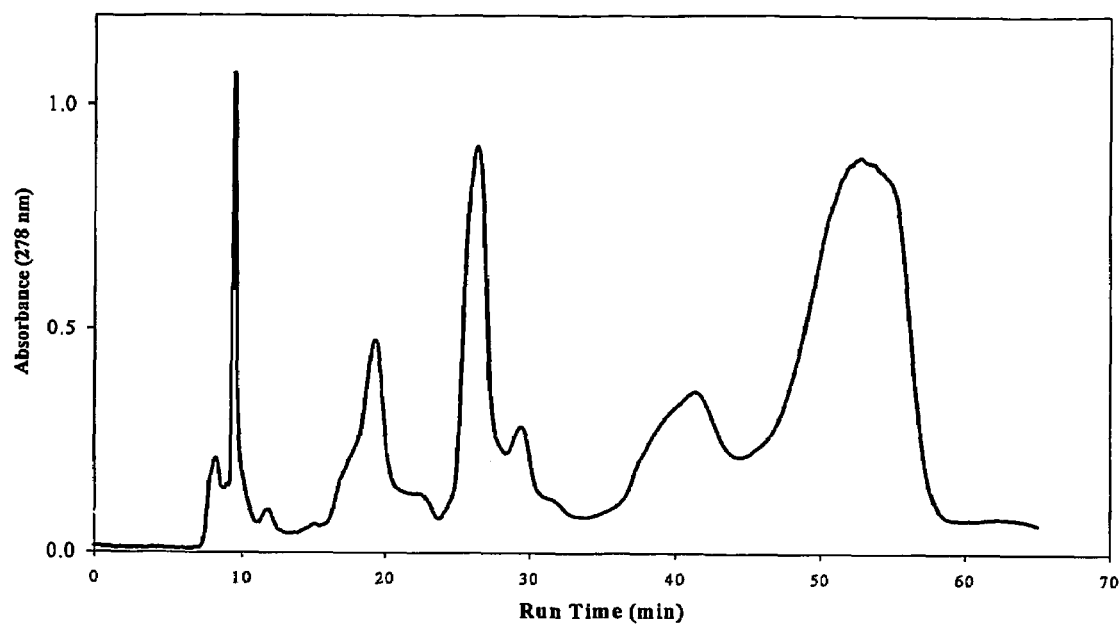
FIGS. 1A and 1B.

When the crude fermentation product of Pneumocandin $B_0$ was first loaded to the HPLC, the resolution of Pneumocandin $B_0$ was limited. Pneumocandin $E_0$ was buried under the peak for Pneumocandin $B_0$ and the separation of Pneumocandin $B_5$ from Pneumocandin $B_0$ was not prominent. See FIG. 1A, which represents the UV (278 nm) traces for the $1^{st}$ run of the silica gel HPLC.

Figure 1B:
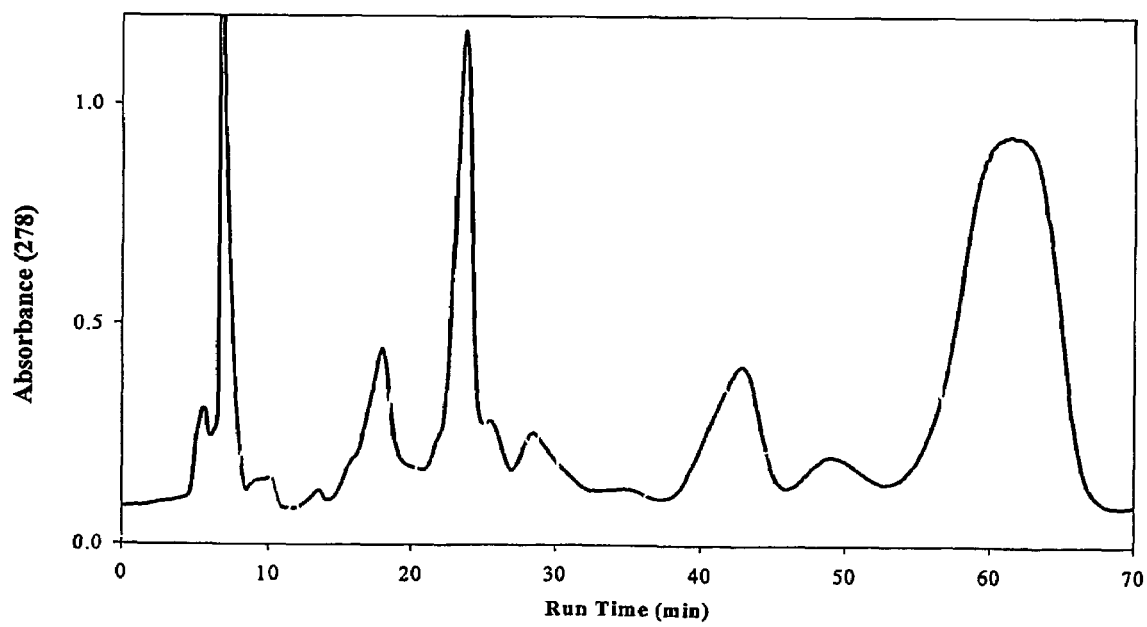

However, after a few sequential HPLC purification runs of this Pneumocandin $B_0$ fermentation product, an increase in the retention time of Pneumocandin $B_0$ by as much as 10 minutes was observed. In addition, Pneumocandin $E_0$, the Pneumocandin $B_0$ that co-eluted in earlier runs was now eluting ahead of the main peak. Furthermore, the resolution of Pneumocandin $B_5$, the close eluter of Pneumocandin $B_0$, improved dramatically. FIG. 1B presents the $18^{th}$ in this series of HPLC runs and clearly shows this increase in retention time and enhanced resolution.

The enhanced separation was reversed by a methanol wash of the column, which was performed every twenty runs for the purpose of removing tightly bound impurities. The improved purification results returned again after a few additional runs. Further investigation determined that the effect was due to the presence of proline in the-column feed (the crude Pneumocandin $B_0$), which adsorbed to the column with each injection. This phenomenon was generalized by addition of proline and related additives to the mobile phase so that the level of the effect could be controlled, providing improvements in resolution and productivity, as described in the examples.

The examples provided herein are intended to assist in a further understanding of the invention. Particular materials, employed species and conditions are intended to be further illustrative of the invention and not limitative of the reasonable scope thereof.

EXAMPLE 1

Figure 2A:
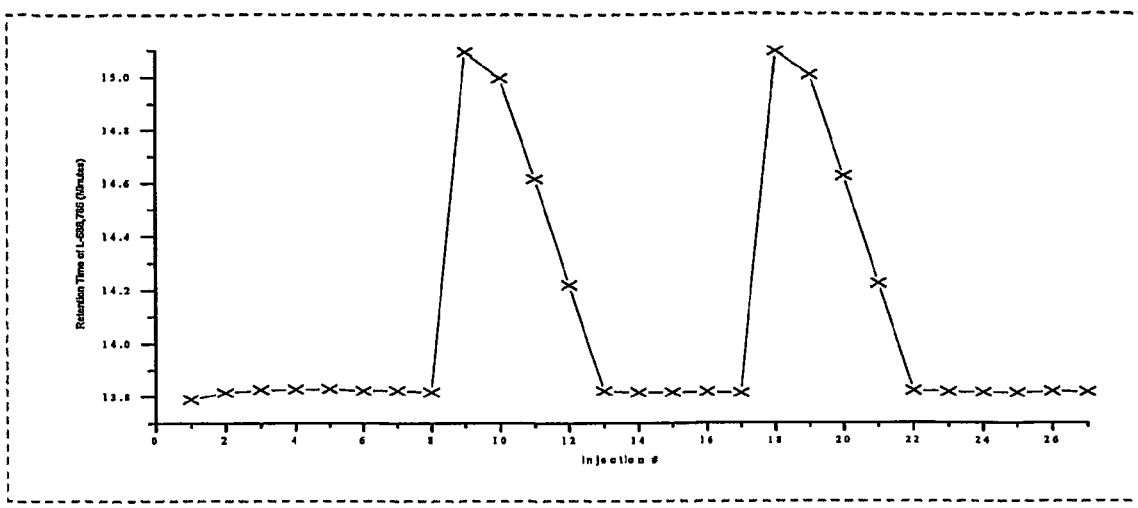
FIGS. 2A, 2B and 2C

On an analytical scale YMC 5 μ silica column using 87/9/7 v/v/v ethyl acetate/methanol/water as the mobile phase, a series of 8 injections of Pneumocandin $B_0$ product containing no L-proline were carried out to establish an unchanging control for comparison. Following this, 10 short injections of an L-proline solution ($1.3 \times 10^{-2}$M L-proline in 79.3/13.3/7.4 v/v/v ethyl acetate/methanol/water, 60 μL injection, about 5 min run time at 1.2 mL/min) were made, and nine additional injections of the Pneumocandin $B_0$ product containing no L-proline were carried out. The procedure was repeated if necessary. FIG. 2A shows the retention time for the Pneumocandin Bo peak in the system for injections made immediately after the series of proline injections, relative to the retention time prior to proline injection. It can be seen that there was a marked increase in retention immediately after L-proline treatment. This was accompanied by an improvement in the selectivity between Pneumocandin $B_0$ and its immediate early eluting peak. However, the retention time returned to normal (RRT~1) after about 5 runs and the improved selectivity was lost, presumably due to the desorption of L-proline with continued elution from the column with the proline-free mobile phase.

Figure 2B:
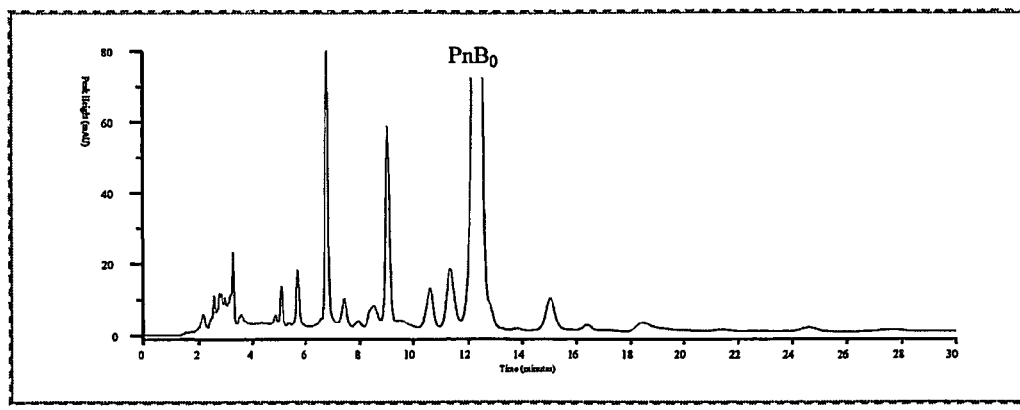
Figure 2C:
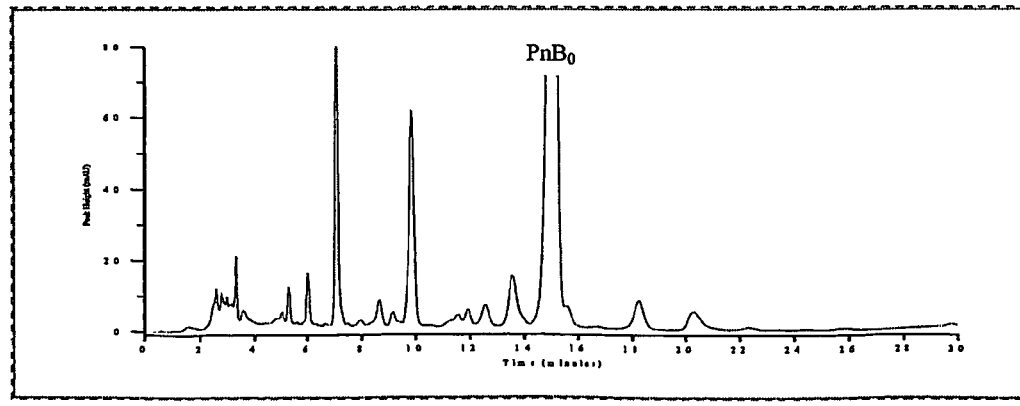

FIGS. 2B and 2C are typical chromatograms obtained from the injections just before and just after the L-proline treatment. The change in retention is apparent, as is a distinct change in resolution between Pneumocandin $B_0$ and Pneumocandins $B_5$ and $E_0$.

EXAMPLE 2

Figure 3A:
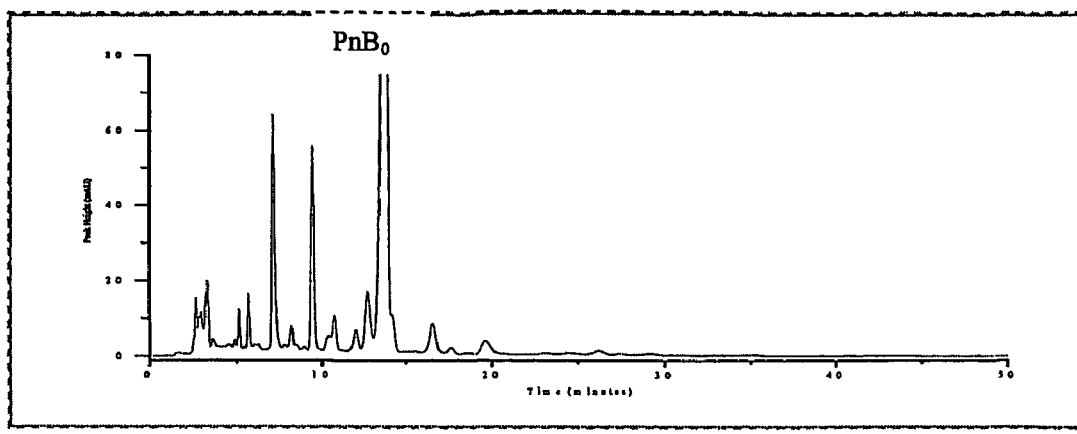
FIGS. 3A, 3B and 3C
Figure 3B:
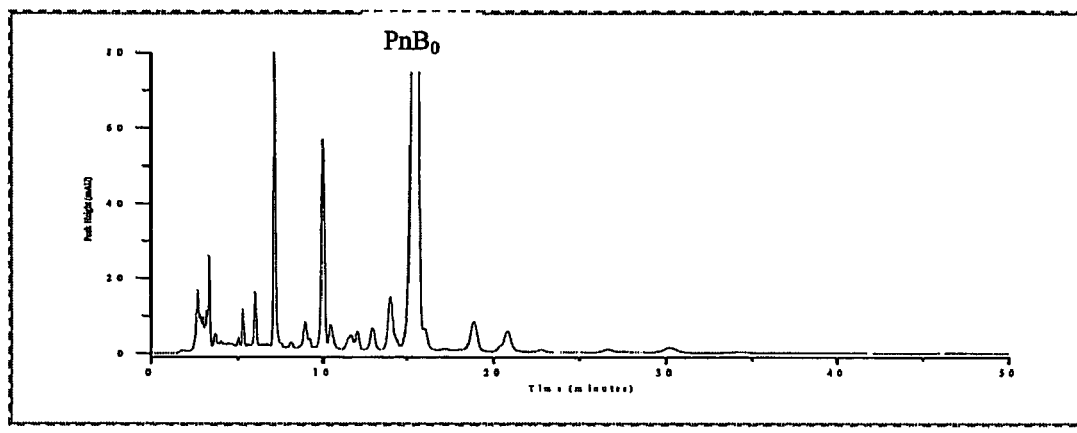
Figure 3C:
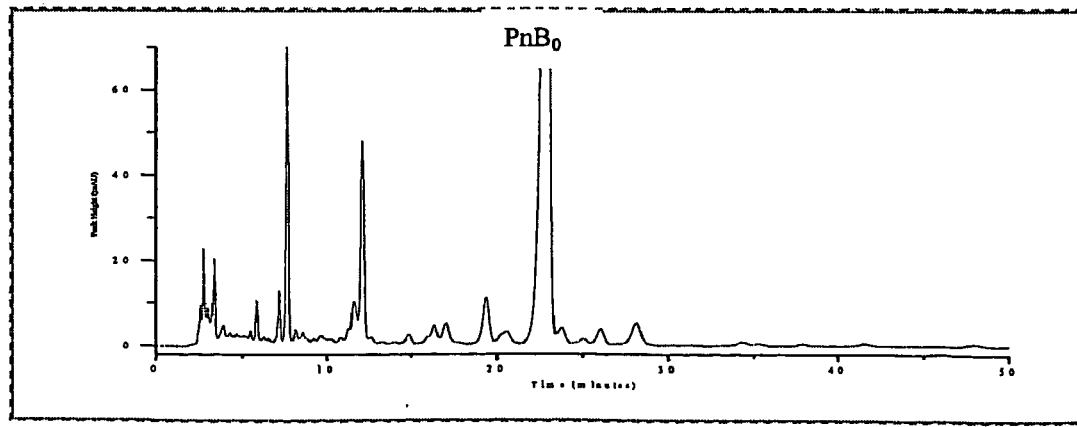

Experiments were carried out on a 5 Tm YMC silica-packed analytical column with L-proline added directly to the mobile phase. FIGS. 3A, B and C shows chromatograms without L-proline and with 0.26 mM (~30 mg/L) and 0.65 mM (~75 mg/L) L-proline in the mobile phase, respectively. The column was equilibrated for 2 hours at 1.2 ml/min with the proline containing mobile phases before the injections were carried out. In FIG. 3C, the peak just ahead of Pneumocandin $B_0$ was determined to be Pneumocandin $E_0$ by the injection of standards Pneumocandin $E_0$ was not separable when the chromatography was carried out without L-proline.

EXAMPLE 3

Figure 4:
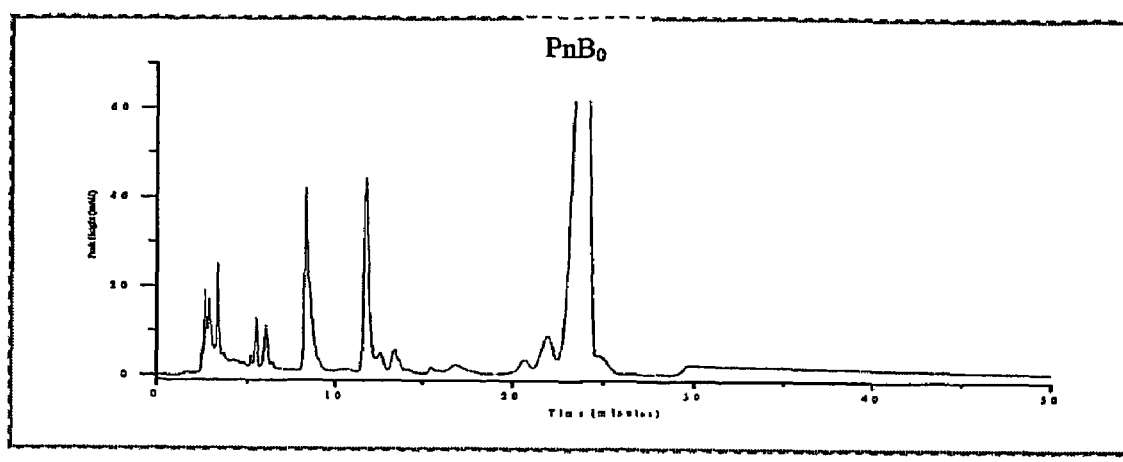

The selectivity enhancement was studied by increasing the retention time of Pneumocandin $B_0$ to around 23 minutes, which is comparable to the retention time of around 22 minutes seen when 0.65 mM L-proline was used in Example 2, by eluting with a mobile phase of 20% ethyl acetate and 80% of the 87/9/7 v/v/v ethyl acetate/methanol/water. Although the retention time of Pneumocandin $B_0$ was increased, Pneumocandin $E_0$ was still buried in the peak of Pneumocandin $B_0$. No enhanced resolution was achieved. See FIG. 4.

EXAMPLE 4

On a semi-preparative scale, a 6 cm ID Prochrom column was packed with 390 g of Amicon Grade 631, 18-20 μ, 60 Å silica (slurried in a 87/9/7 v/v/v water/ethyl acetate/methanol (WEAM) mobile phase; packing pressure 40 bar; column length 25 cm) was used.

Benchmark Run:

A feed solution was prepared by dissolving 90 g of crude Pneumocandin $B_0$ without L-proline in 1.5 L feed solvent (79.3/13.3/7.4 v/v/v ethyl acetate/methanol/water) giving a 34.9 assay g/L Pneumocandin $B_0$ feed solution. In order to establish a control for the experiment, 80 mL of the feed (2.8 g Pneumocandin $B_0$) were injected and eluted with the WEAM mobile phase at a flow rate of 90 mL/min. Fractions were collected from this run and analytical results of a pooled representative rich cut indicated that the impurity profile was consistent with previous batches (by both normal phase (NP) and reversed phase (RP) HPLC assays).

Runs with L-proline in the Mobile Phase (Similar Load to Benchmark):

The WEAM mobile phase was modified with L-proline at a concentration of 75 mg/L (0.650 mM). The column was conditioned with 5 column volumes (CV) of this solution and a run was carried out with the modified mobile phase under conditions otherwise similar to the benchmark runs. The shift in retention time observed in this system was not as dramatic as in the analytical system. Table 2 summarizes the impurity profiles of the rich cuts from the two runs: levels of Pneumocandin $B_5$ and Pneumocandin $E_0$ are dramatically lower in the proline modified run, showing that higher throughputs could be achieved with this system.

TABLE 2

Summary of rich cut impurity profiles from laboratory runs, standard loading, without and with 0.15 g/L (1.3 M) of L-proline in the mobile phase

| Run | Load as grams Pneumocandin $B_0$ per kg silica | Pn $B_5$ % Area | Pn $E_0$ % Area | Yield % | Mass Balance % |
|---|---|---|---|---|---|
| Benchmark run | 7.2 | 0.44 | 0.42 | 82 | 99 |
| L-proline system | 7.2 | 0.16 | 0.05 | 84 | 98 |

Doubling Column Throughput with the L-proline Modified Mobile Phase:

A run was carried out using the proline-modified system described above with double the benchmark load: 5.6 g Pneumocandin $B_0$ injected (14.4 g/kg silica) by doubling the volume of the feed solution injected, all other conditions being the same. The impurity profile of the rich cut, as well as the yield and mass balance, is summarized in Table 3. The results indicate the potential use of this method to double the productivity of the chromatography step, since in this example the yield has been maintained while increasing purity at double the benchmark loading.

TABLE 3

Summary of rich cut impurity profiles from laboratory runs, 2× loading, without and with 0.075 g/L (0.65 M) and 0.15 g/L (1.3 M) L-proline in the mobile phase

| Run | Load: g Pneumocandin $B_0$ per kg silica | Pn $B_5$ % Area | Pn $E_0$ % Area | Yield (%) | Mass Balance (%) |
|---|---|---|---|---|---|
| Benchmark | 7.2 | 0.44 | 0.42 | 82 | 99 |
| L-proline system | 7.2 | 0.16 | 0.05 | 84 | 98 |
| L-proline system | 14.4 | 0.27 | 0.08 | 86 | 99 |

EXAMPLE 6

Other Amino Acids as Mobile Phase Modifiers

In order to obtain further insight regarding the phenomenon, a series of analytical experiments were carried out using a 25×0.46 cm YMC 5 μ silica column with a wide variety of amino acid modifiers, including trans-4-hydroxy-L-proline, L-valine, L-lysine, L-methionine, D-proline, L-threonine and glycine in the mobile phase at a concentration of 0.65 mM. See FIGS. 5-11.

Table 4 sorts the amino acids in order of decreasing retention. FIGS. 5 through 10 provide exemplary chromatograms obtained from these runs that illustrate their various effects on retention time and selectivity. With every amino acid except 4-hydroxy-L-proline, retention increased compared to the amino acid-free case, and the selectivity was modified uniquely in each instance. For example, although trans-4-hydroxy-L-proline did not cause the retention of Pneumocandin $B_0$ to shift, it did affect the resolution of Pneumocandin $B_0$ from the early eluting peak, as seen in FIG. 5.

Glycine has no side chain, but it also increases the retention time. This strongly suggests that the retention time shift and the improved resolution is not the unique effect of the amino acid side chain.

L-proline methyl ester was employed, in place of an amino acid and had an increased retention time (retention time of Pneumocandin $B_0$ relative to the control was 1.65) and a change in selectivity.

After each set of 3 or 4 runs with a particular amino acid, the column was washed with 36 ml (~8 column volumes, hereinafter referred to as CV) of methanol and then re-equilibrated with 10 CV of neat WEAM mobile phase, after which three (~30 min) injections were carried out to confirm that the amino acid had been removed (i.e., that baseline performance had been recovered). Following this, the column was re-conditioned with 72 mL (~17 CV) of the mobile phase containing a new amino acid, and new injections were then made. The retention times reported are for the 3$^{rd}$ run in each case. Since it is unclear what the saturation capacity of the silica is for the different amino acids, this protocol ensured that in each case the column had been exposed to the same number of moles of the amino acid. The column could not be adequately regenerated after exposure to L-lysine (which was purposely tested as the last amino acid), presumably due to the two primary amines.

TABLE 4

Retention times of Pneumocandin $B_0$ on a YMC 5μ, 120 Å, silica column 25 cm × 0.46 cm ID at a flow rate of 1.2 mL/min.

| Amino Acid (65 mM) in WEAM | Retention of Pneumocandin $B_0$ relative to the control |
|---|---|
| L-proline methyl ester | 1.65 |
| L-proline | 1.44 |
| Glycine | 1.38 |
| L-threonine | 1.35 |
| D-proline | 1.25 |
| L-methionine | 1.16 |
| L-lysine | 1.13 |
| L-valine | 1.10 |
| trans-4-hydroxy-L-proline | 1.00 |
| None (control) | 1.00 |

EXAMPLE 7

Chromatography with Diethylamine as a Mobile Phase Modifier

Diethylamine was added to the mobile phase at about 0.1 g/L, and the experimental conditions were identical to that employed previously in Example 6. As shown in FIG. 12, the retention time increased even more with diethylamine than with proline. Therefore, the influence on retention and selectivity appears to be mediated by the amine functionality, such that either an amine or an amino acid/amino acid ester could be used as a mobile phase modifier in this system.

What is claimed is:

1. A method of purifying a peptide or a lipopeptide by using a mobile phase modifier in a normal phase chromatography system to improve the selectivity and/or productivity of the purification, wherein the mobile phase modifier is selected from a group consisting of an amino acid and an amino acid ester, the normal phase chromatography system includes a mobile phase and a stationary phase, the mobile phase is a solvent system comprising one or more solvents, and the stationary phase is selected from silica gel and alumina, except that when the lipopeptide is Pneumocandin $B_0$, then the mobile phase modifier is not L-proline.

2. The method as recited in claim 1, wherein the amino acid or amino acid ester mobile phase modifier is selected from the group consisting of: L-amino acids, D-amino acids, L-amino acid esters and D-amino acid esters.

3. The method as recited in claim 2, wherein the amino acid or amino acid ester mobile phase modifier is selected from: L-proline, D-proline, trans-4-hydroxy-L-proline, trans-4-hydroxy-D-proline, glycine, L-threonine, D-threonine, L-lysine, D-lysine, L-methionine, D-methionine, D-valine, L-valine and esters of the aforementioned L-and D-amino acids.

4. The method as recited in claim 3, wherein the amino acid is selected from: L-proline and D-proline.

5. The method as recited in claim 1, wherein the normal phase chromatography system is for the purification of a peptide.

6. The method as recited in claim 5, wherein the peptide is oxytocin or bradykinin.

7. The method as recited in claim 1, wherein the normal phase chromatography system is for the purification of a lipopeptide.

8. The method as recited in claim 7, wherein the lipopeptide is a fermentation product precursor of caspofungin, micafungin, cilofungin, andulifungin and daptomycin.

9. The method as recited in claim 8, wherein the fermentation product precursor of caspofungin is pneumocandin $B_0$.

10. The method as recited in claim 9, wherein the amino acid or amino acid ester mobile phase modifier is selected from the group consisting of: L-amino acids, D-amino acids, L-amino acid esters and D-amino acid esters, except the L-amino acid is not L-proline.

11. The method as recited in claim 10, wherein the amino acid or amino acid ester mobile phase modifier is selected from: D-proline, trans-4-hydroxy-L-proline, trans-4-hydroxy-D-proline, glycine, L-threonine, D-threonine, L-lysine, D-lysine, L-methionine, D-methionine, D-valine, L-valine and esters of the aforementioned L-and D-amino acids.

12. The method as recited in claim 11, wherein the amino acid mobile phase modifier is D-proline.

13. The method as recited in claim 1, wherein the mobile phase is a solvent system comprising water, methanol, and ethyl acetate.

14. The method as in claim 1, wherein the stationary phase is silica gel.

15. A method of purifying pneumocandin $B_0$ by using a mobile phase modifier in a normal phase chromatography system to improve the selectivity and/or productivity of the purification, wherein the normal phase chromatography system includes a mobile phase and a stationary phase, the mobile phase is a solvent system comprising one or more solvents, the stationary phase is selected from silica gel and alumina, and the mobile phase modifier is selected from the group consisting of: methylamine, ethylamine, diisopropylamine, diethylamine, dimethylamine, ethylmethylamine, triethylamine, propylamine, aniline and dimethylaniline.

16. The method as in claim 15, wherein the stationary phase is silica gel.

17. A method of purifying oxytocin or bradykinin by using a mobile phase modifier in a normal phase chromatography system to improve the selectivity and/or productivity of the purification, wherein the normal phase chromatography system includes a mobile phase and a stationary phase, the mobile phase is a solvent system comprising one or more solvents, the stationary phase is selected from silica gel and alumina, and the mobile phase modifier is selected from the group consisting of: methylamine, ethylamine, diisopropylamine, diethylamine, dimethylamine, ethylmethylamine, triethylamine, propylamine, aniline and dimethylaniline.

* * * * *